United States Patent
Brady-Kalnay

(10) Patent No.: US 10,632,179 B2
(45) Date of Patent: Apr. 28, 2020

(54) METHODS AND COMPOSITIONS FOR TREATING CANCER

(71) Applicant: Case Western Reserve University, Cleveland, OH (US)

(72) Inventor: Susann Brady-Kalnay, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 14/760,672

(22) PCT Filed: Jan. 13, 2014

(86) PCT No.: PCT/US2014/011289
§ 371 (c)(1),
(2) Date: Jul. 13, 2015

(87) PCT Pub. No.: WO2014/110503
PCT Pub. Date: Jul. 17, 2014

(65) Prior Publication Data
US 2015/0352192 A1     Dec. 10, 2015

Related U.S. Application Data

(60) Provisional application No. 61/751,332, filed on Jan. 11, 2013.

(51) Int. Cl.
| | | |
|---|---|---|
| *A61K 38/00* | (2006.01) | |
| *A61K 38/17* | (2006.01) | |
| *C07K 14/435* | (2006.01) | |
| *C07K 14/705* | (2006.01) | |
| *C07K 14/735* | (2006.01) | |
| *A61K 38/46* | (2006.01) | |
| *A61K 45/06* | (2006.01) | |
| *A61N 5/10* | (2006.01) | |
| *C12N 9/50* | (2006.01) | |

(52) U.S. Cl.
CPC ............ *A61K 38/465* (2013.01); *A61K 45/06* (2013.01); *A61N 5/10* (2013.01); *C12N 9/50* (2013.01); *C12Y 301/03048* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 9,241,949 B2 * | 1/2016 | Brady-Kalnay ... | A61K 31/7105 |
| 2004/0044188 A1 * | 3/2004 | Feige ................... | C07K 14/505 |
| | | | 530/388.23 |
| 2013/0287702 A1 * | 10/2013 | Brady-Kalnay ... | A61K 49/0058 |
| | | | 424/9.6 |
| 2016/0083734 A1 * | 3/2016 | Brady-Kalnay ... | A61K 31/7105 |
| | | | 514/19.8 |

FOREIGN PATENT DOCUMENTS

| | | |
|---|---|---|
| EP | 2407173 A1 | 1/2012 |
| WO | 2010019884 A1 | 2/2010 |
| WO | 2011020090 A2 | 2/2011 |

OTHER PUBLICATIONS

Streuli et al. (EMBO Journal, 1992, 11:897-907).*
Arlt et al. (Cancer Research, 2006, 66:936-943).*
Gavert et al. (Expert Opinion on Biological Therapy, 2008, 8:1749-1757).*
Ping-Hui Sun, et al., Protein Tyrosine Phosphatase μ (PTP μ or PTPRM), a Negative Regulator of Proliferation and Invasion of Breast Cancer Cells, Is Associated with Disease Prognosis. PLOS ONE, 2012, vol. 7, Issue I I, e50183, doi:10.1371/journal.pone.0050183.
Harpreet Kaur et al. Protein tyrosine phosphatase mu regulates glioblastoma cell growth and survival in vivo. Neuro-Oncology, 2012, 14 (5), pp. 561-573.
Adam M. Burgoyne et al. Proteolytic Cleavage of Protein Tyrosine Phosphatase μ Regulates Glioblastoma Cell Migration. Cancer Res., 2009, 69: (17), pp. 6960-6968.
Phillips-Mason PJ et al. Should I stay or should I go? Shedding of RPTPs in cancer cells switches signals from stabilizing cell-cell adhesion to driving cell migration. Cell Adhesion & Migration, 2011, vol. 5, No. 4, pp. 298-305.
Craig S.E. et al. Cancer cells cut homophilic cell adhesion molecules and run. Cancer Res., 2011, vol. 71, No. 2, pp. 303-309. doi:10.1158/0008-5472.CAN-10-2301, pp. 1-11.

* cited by examiner

*Primary Examiner* — Julie Wu
(74) *Attorney, Agent, or Firm* — Tarolli, Sundheim, Covell & Tummino LLP

(57) ABSTRACT

A method of treating cancer in a subject includes administering to the subject a therapeutically effective amount of an agent that specifically binds to or complexes with a proteolytically cleaved extracellular fragment of an immunoglobulin (Ig) superfamily cell adhesion molecule (CAM) or its receptor that is expressed by a cancer cell or another cell in the cancer cell microenvironment. The agent inhibits the cell adhesion function of the cleaved extracellular fragment or its receptor.

11 Claims, 6 Drawing Sheets

Specification includes a Sequence Listing.

Treatment of CNS-1-GFP flank tumors with SBK2 or Scrambled probes
A
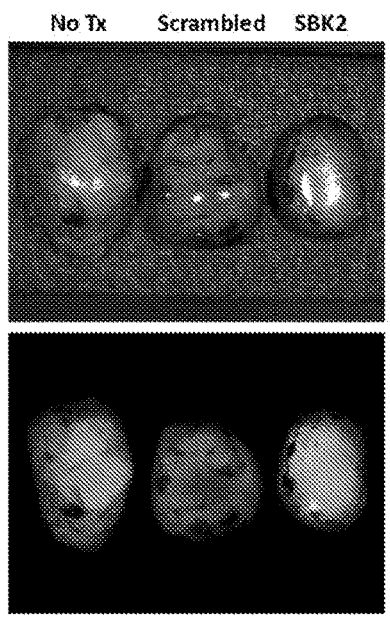
B
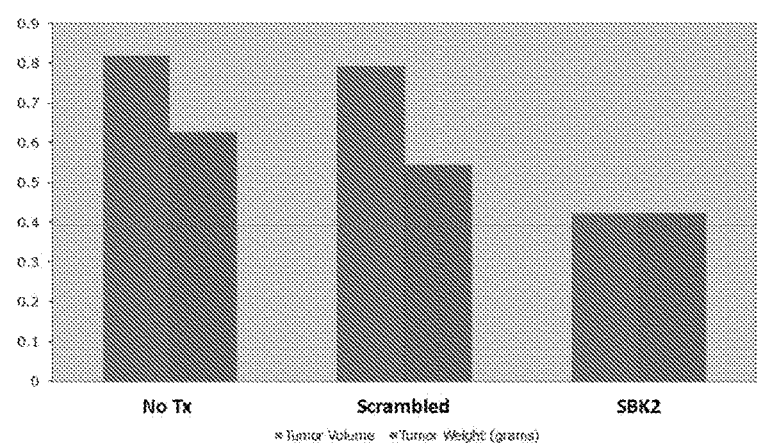
Figs. 2A-B

METHODS AND COMPOSITIONS FOR TREATING CANCER

RELATED APPLICATION

This application claims priority from U.S. Provisional Application No. 61/751,332, filed Jan. 11, 2013, the subject matter of which is incorporated herein by reference in its entirety.

BACKGROUND

Cancer is a worldwide problem. Finding novel compositions and methods for the treatment of cancer is of vital interest. The treatment of cancer falls into three general categories: chemotherapy, radiation therapy and surgery. Often, therapies are combined since a combination of therapies increases the probability the cancer will be eradicated as compared to treatment strategies utilizing a single therapy. Typically, the surgical excision of large tumor masses is followed by chemotherapy and/or radiation therapy.

Cancer starts as a primary tumor at a single location. The primary tumor rarely causes death as it is usually surgically removed. Once cancer cells move away from the primary tumor site (migration, dispersal, and invasion) and move to distant sites (metastasis) the cancer becomes more deadly. The migrating, dispersing, and invading cancer cells can rarely be detected and must be treated by conventional chemotherapy. Conventional chemotherapy does not specifically target cancer cells but affects a number of rapidly dividing normal cells.

SUMMARY

Embodiments described herein relate to compositions and methods of treating cancer in a subject. The methods can include administering to the subject a therapeutically effective amount of an agent that specifically binds to or complexes with a proteolytically cleaved extracellular fragment of an immunoglobulin (Ig) superfamily cell adhesion molecule (CAM) or its receptor that is expressed by a cancer cell or another cell in the cancer cell microenvironment.

In some embodiments, the agent can inhibit the cell adhesion function of the cleaved extracellular fragment or its receptor. The cell adhesion function can include heterophilic or homophilic binding of the extracellular fragment or its receptor, and the agent can inhibit binding of the extracellular fragment to its receptor.

In other embodiments, the Ig superfamily CAM can be a receptor protein tyrosine phosphatase (RPTP) that is proteolytically cleaved to form the extracellular fragment. For example, the RPTP molecule can be PTPµ.

In yet other embodiments, the cancer cell can be one or more of, a migratory, dispersive, invasive and metastatic cancer cell in a subject, and the agent can inhibit migration, dispersal, invasion or metastasis of the cancer. For example, the cancer cell can include at least one of a glioma, lung cancer, melanoma, or prostate cancer cell. The proteolytically cleaved extracellular fragment of an Ig superfamily CAM can also be expressed by another cell, such as a stem cell, endothelial cell, stromal cell or immune cell, that supports survival of the cancer cell.

In some embodiments, the extracellular fragment can include an amino acid sequence of SEQ ID NO: 2, and the agent can specifically bind to an extracellular fragment having an amino acid sequence of SEQ ID NO: 2. For example, the agent can include a polypeptide that specifically binds to an amino acid sequence of SEQ ID NO: 2. The agent can also include a polypeptide having an amino acid sequence that is substantially homologous to about 10 to about 50 consecutive amino acids of SEQ ID NO: 3. The agent can further include a polypeptide having an amino acid sequence selected from the group consisting of SEQ ID NO: 4, SEQ ID NO: 5, SEQ ID NO: 6, SEQ ID NO: 7, SEQ ID NO: 8, SEQ ID NO: 11, and SEQ ID NO: 12.

In other embodiments, the agent can include an antibody or fragment thereof that specifically binds to the extracellular fragment or its receptor. The agent can also include a polypeptide-Fc chimera. The polypeptide portion of the polypeptide-Fc chimera can specifically bind to the extracellular fragment or its receptor. The polypeptide of the polypeptide-Fc chimera can also include an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 11, and SEQ ID NO: 12. The Fc portion of the polypeptide-Fc chimera can have an amino acid sequence of SEQ ID NO: 9. The Fc can contain the hinge region of IgG1 or IgG4 fused to the CH2 and CH3 domains of human IgG1. The polypeptide-Fc chimera can also include a linking molecule, which is not a contiguous portion of either the polypeptide or Fc and which covalently joins an amino acid of the polypeptide to an amino acid of Fc.

In yet other embodiments, the therapeutic agent can include a detectable moiety. The therapeutic agent can be detected in vivo by recognizing the detectable moiety. The detectable moiety can be detected by, for example, at least one of gamma imaging, positron emission tomography (PET) imaging, computer tomography (CT) imaging, magnetic resonance imaging, near infrared imaging, or fluorescent imaging.

The therapeutic agent with the detectable moiety when used in the methods described herein can be detected upon administration to the subject to measure the efficacy of the therapeutic agent in treating the cancer in the subject. For example, a therapeutically effective amount of an agent that specifically binds to or complexes with a proteolytically cleaved extracellular fragment of an Ig superfamily CAM or its receptor that is expressed by a cancer cell or another cell in the cancer cell microenvironment and that includes a detectable moiety can be administered to the subject to treat cancer. The therapeutic agent bound to and/or complexed with the proteolytically cleaved extracellular fragment of the Ig superfamily cell adhesion molecule can then be detected in the subject to provide the location and/or distribution of the cancer cells in the subject. The location and/or distribution of the cancer cells in subject can be monitored over time by, for example, subsequent administrations of the therapeutic agent to determine efficacy of the therapeutic agent in treating the cancer.

Embodiments described herein also relate to a composition for treating cancer. The composition can include a polypeptide-Fc chimera that specifically binds to or complexes with a proteolytically cleaved extracellular fragment of an Ig superfamily CAM or its receptor that is expressed by a cancer cell or another cell in the cancer cell microenvironment. The polypeptide-Fc chimera inhibits cell adhesion function of the cleaved extracellular fragment or its receptor. The polypeptide portion of the polypeptide-Fc chimera can include an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 11, and SEQ ID NO: 12. The Fc portion of the polypeptide-Fc chimera can include an amino acid sequence of SEQ ID NO: 9. The polypeptide-Fc chimera can also include a linking molecule, which is not a contiguous portion of either the polypeptide or Fc and which covalently joins an amino acid of the polypeptide to an amino acid of Fc.

In some embodiments, the polypeptide-Fc chimera can include a detectable moiety. The polypeptide-Fc can be detected in vivo by recognizing the detectable moiety. The detectable moiety can be detected by, for example, at least one of gamma imaging, positron emission tomography (PET) imaging, computer tomography (CT) imaging, magnetic resonance imaging, near infrared imaging, or fluorescent imaging. The polypeptide-Fc chimera with the detectable moiety when used in the methods described herein can be detected upon administration to the subject to measure the efficacy of the polypeptide-Fc chimera in treating the cancer in the subject.

In still other embodiments, methods of treating cancer in a subject can include first obtaining a sample or biopsy of cells and/or tissue including or suspected of including cancer cells from the subject. The biopsied cells and/or tissue is then assayed to determine if the biopsied cells and/or tissue includes cancer cells expressing an Ig superfamily cell adhesion molecule, such as PTPμ, which has been proteolytically cleaved to form a extracellular fragment. For example, the biopsied cells and/or tissue can be contacted with a molecular probe that detects whether biopsied cells and/or tissue includes a proteolytically cleaved extracellular fragment of the Ig superfamily CAM. A therapeutically effective amount of an agent that specifically binds to or complexes with a proteolytically cleaved extracellular fragment of an Ig superfamily CAM or its receptor that is expressed by a cancer cell or another cell in the cancer cell microenvironment is then administered to the subject to treat the cancer if the proteolytically cleaved extracellular fragments of the Ig superfamily CAM are detected in the sample or biopsy.

In some embodiments, the agent can inhibit the cell adhesion function of the cleaved extracellular fragment or its receptor. The cell adhesion function can include heterophilic or homophilic binding of the extracellular fragment or its receptor, and the agent can inhibit binding of the extracellular fragment to its receptor.

In other embodiments, the Ig superfamily CAM can be a receptor protein tyrosine phosphatase (RPTP) that is proteolytically cleaved to form the extracellular fragment. For example, the RPTP molecule can be PTPμ.

In yet other embodiments, the cancer cell can be one or more of, a migratory, dispersive, invasive and metastatic cancer cell in a subject, and the agent can inhibit migration, dispersal, invasion or metastasis of the cancer. For example, the cancer cell can include at least one of a glioma, lung cancer, melanoma, or prostate cancer cell. The proteolytically cleaved extracellular fragment of an immunoglobulin (Ig) superfamily CAM can also be expressed by another cell, such as a stem cell, endothelial cell, stromal cell or immune cell, that supports survival of the cancer cell.

In some embodiments, the extracellular fragment can include an amino acid sequence of SEQ ID NO: 2, and the agent can specifically bind to an extracellular fragment having an amino acid sequence of SEQ ID NO: 2. For example, the agent can include a polypeptide that specifically binds to an amino acid sequence of SEQ ID NO: 2. The agent can also include a polypeptide having an amino acid sequence that is substantially homologous to about 10 to about 50 consecutive amino acids of SEQ ID NO: 3. The agent can further include a polypeptide having an amino acid sequence selected from the group consisting of SEQ ID NO: 4, SEQ ID NO: 5, SEQ ID NO: 6, SEQ ID NO: 7, SEQ ID NO: 8, SEQ ID NO: 11, and SEQ ID NO: 12.

BRIEF DESCRIPTION OF THE DRAWINGS

FIGS. 2(A-B) illustrate (A) images heterotopic xenograft flank tumors of mice intravenously administered a scrambled control polypeptide or a therapeutic polypeptide, SBK2 with an additional glycine residue (SEQ ID NO: 11), and (B) a graph showing the weight and volume of flank tumors of the mice intravenously administered the scrambled and control polypeptide.

DETAILED DESCRIPTION

Figure 1:
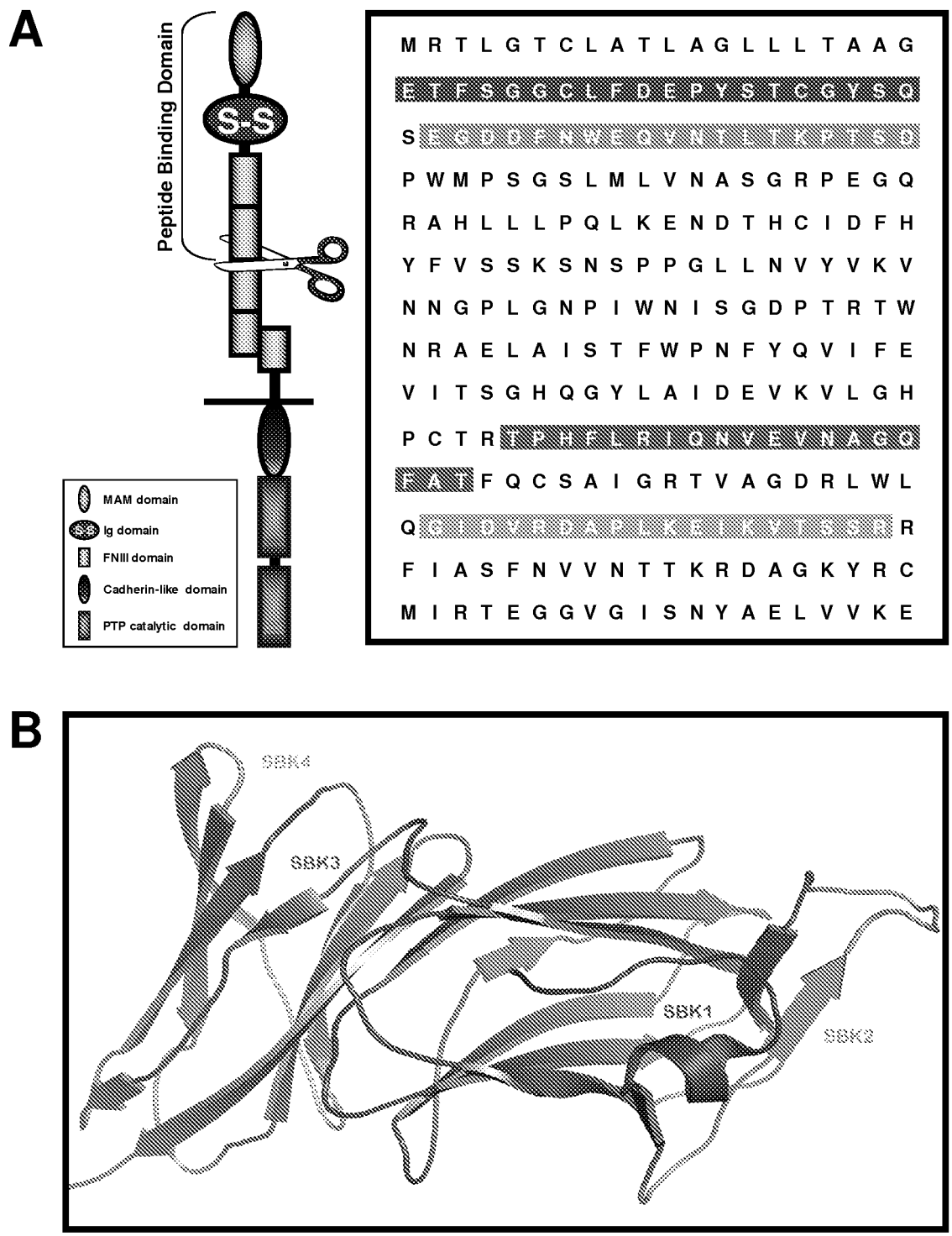
FIG. 1 is a schematic illustration of a PTPμ structure and therapeutic peptide sequences. The scissors indicate one potential site in the FNIII domain where PTPμ can be cleaved to generate a 55 kDa N-terminal fragment. It will be appreciated that that PTPμ can be cleaved at other sites in the FNIII domain. The sequence is shown for the PTPμ MAM, Ig, and FNIII domains (i.e., SEQ ID NO: 3). The highlighted regions indicate the sequences used to generate PTPμ therapeutic peptide (i.e., SBK1 (SEQ ID NO: 4), SBK2 (SEQ ID NO: 5), SBK3 (SEQ ID NO: 6), and SBK4 (SEQ ID NO: 7). (B) Crystal structure of the Ig and MAM domains of PTPμ (PDB ID: 2V5Y). SBK1 (SEQ ID NO: 4) and SBK2 (SEQ ID NO: 5) were derived from the N-terminal MAM domain while SBK3 (SEQ ID NO: 6) and SBK4 (SEQ ID NO: 7) were from the Ig domain.
Figure 3A:
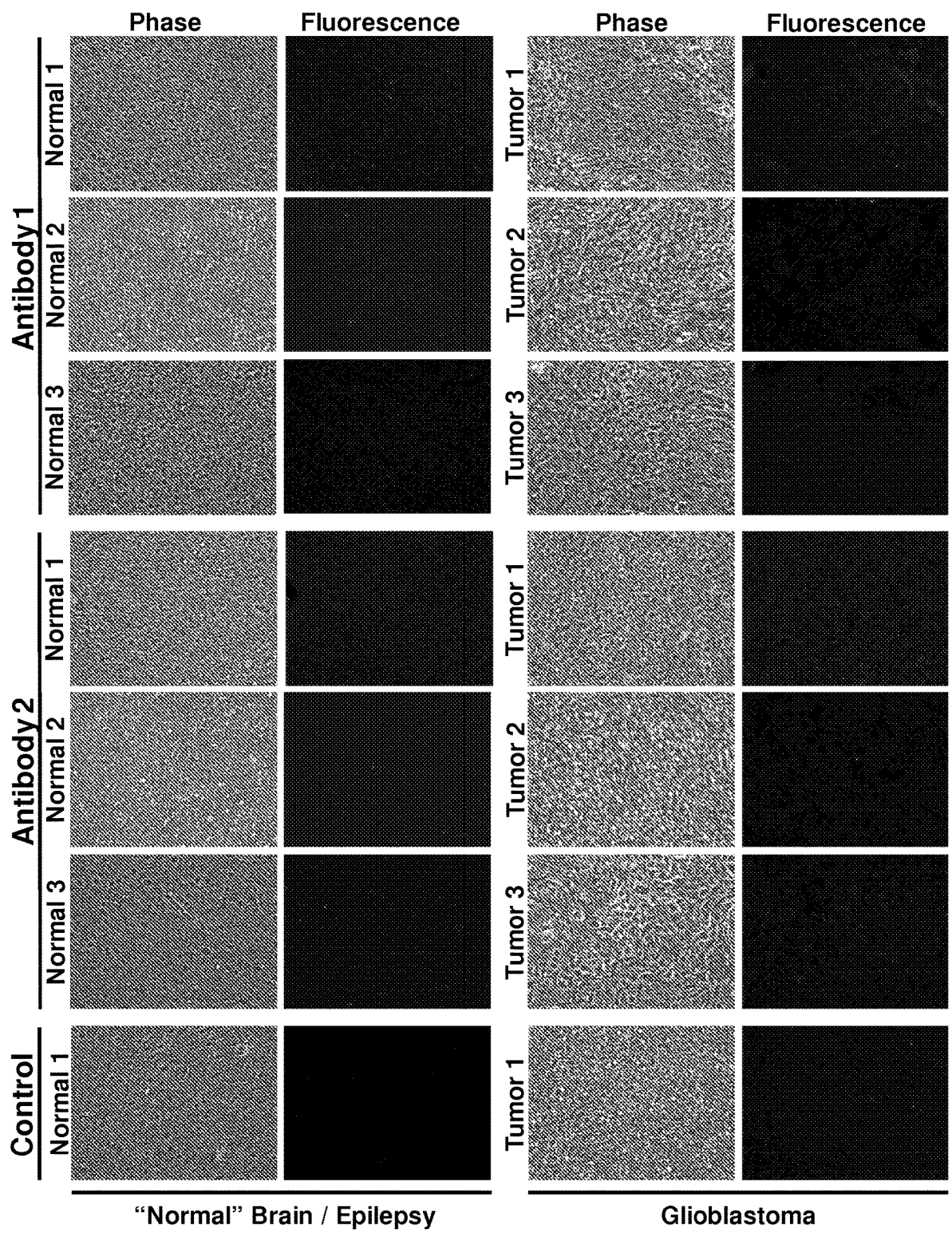
FIG. 3(A-D) illustrates images showing sections of non-cancerous normal cortical brain tissue from epilepsy patients and GBM tumors labeled with a series of anti-PTPμ antibodies (Antibodies 1-7) and visualized with Alexa Flour 568 secondary antibody. Only a subset of the antibodies was able to recognize the PTPμ fragment in the GBM tumor tissue.
Figure 3B:
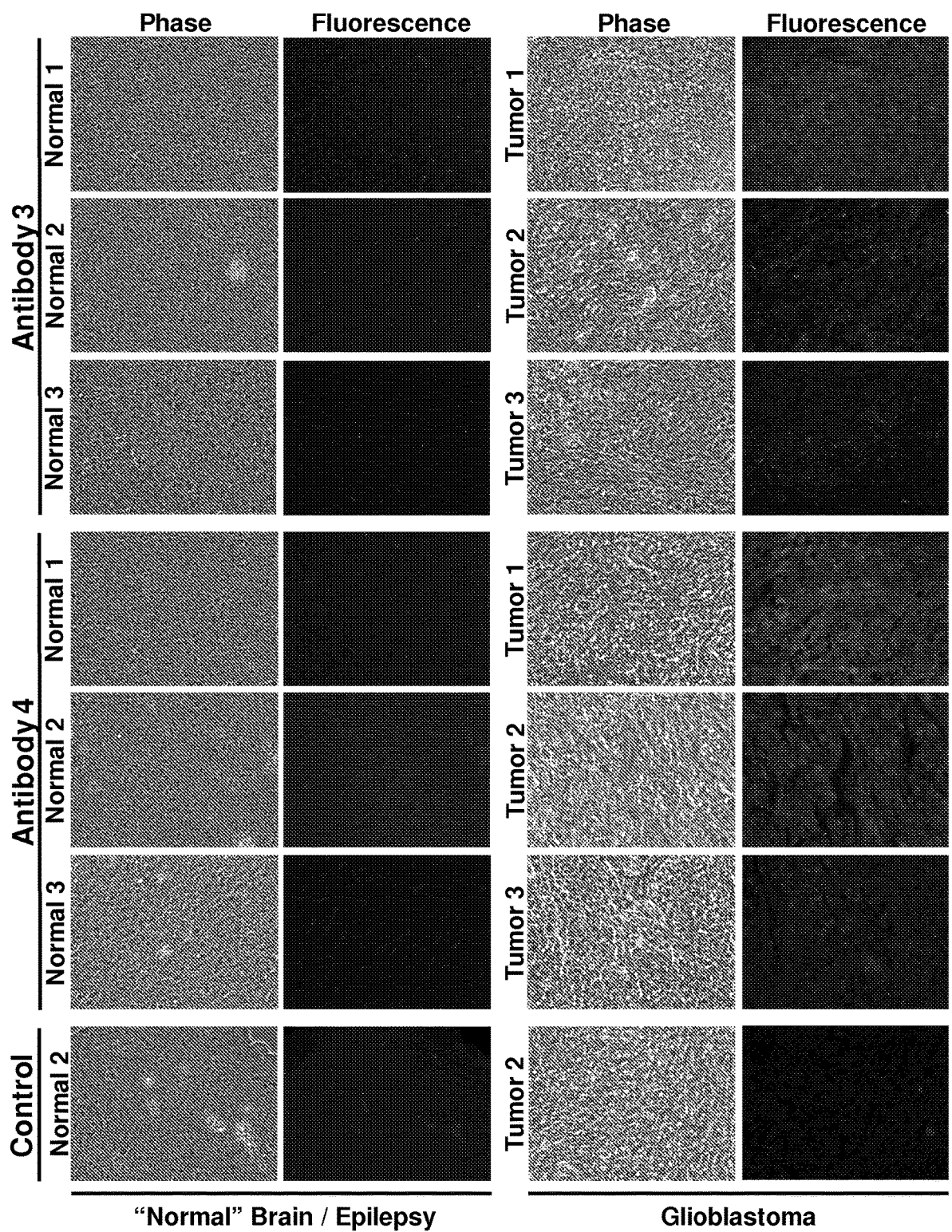
Figure 3C:
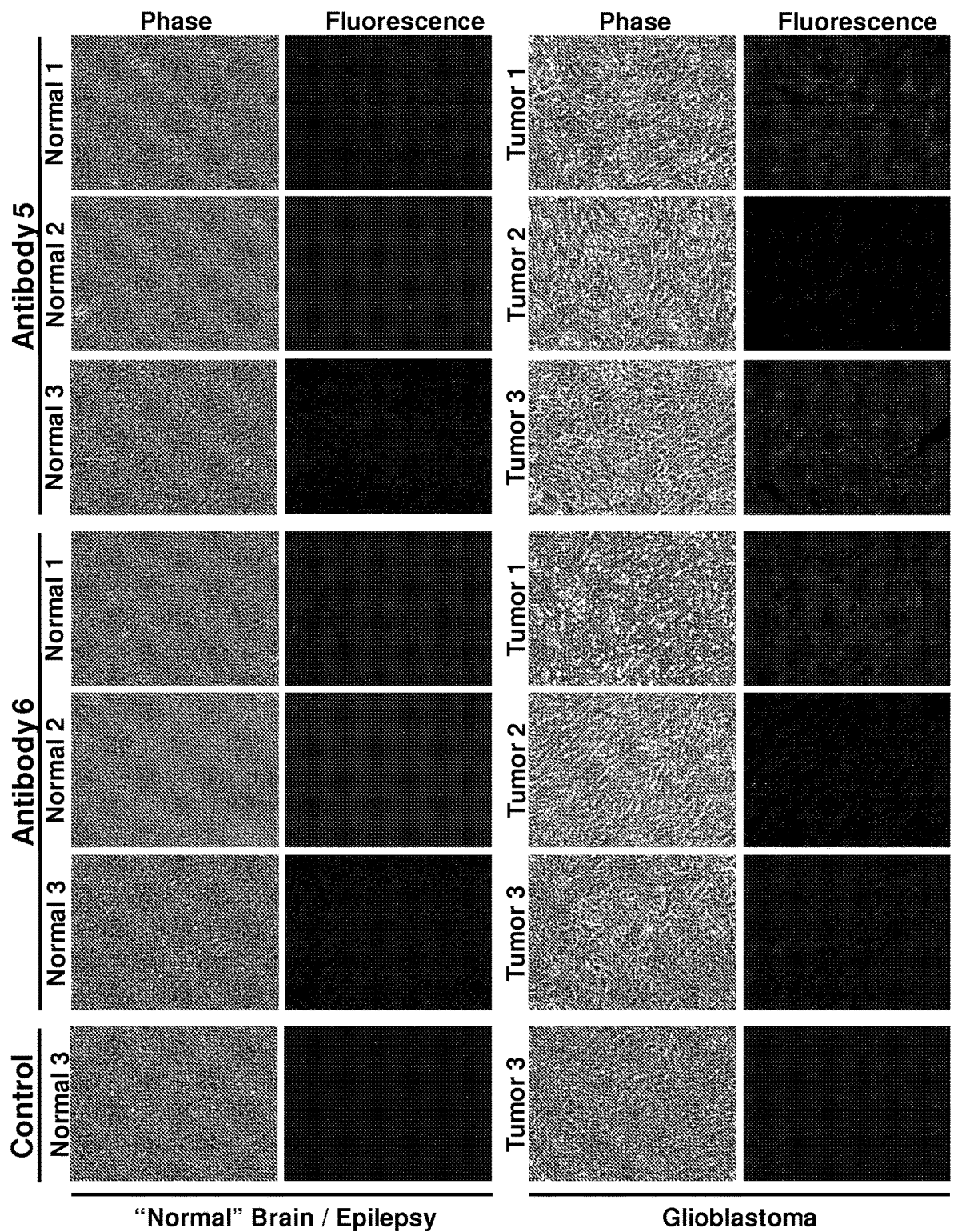
Figure 3D:
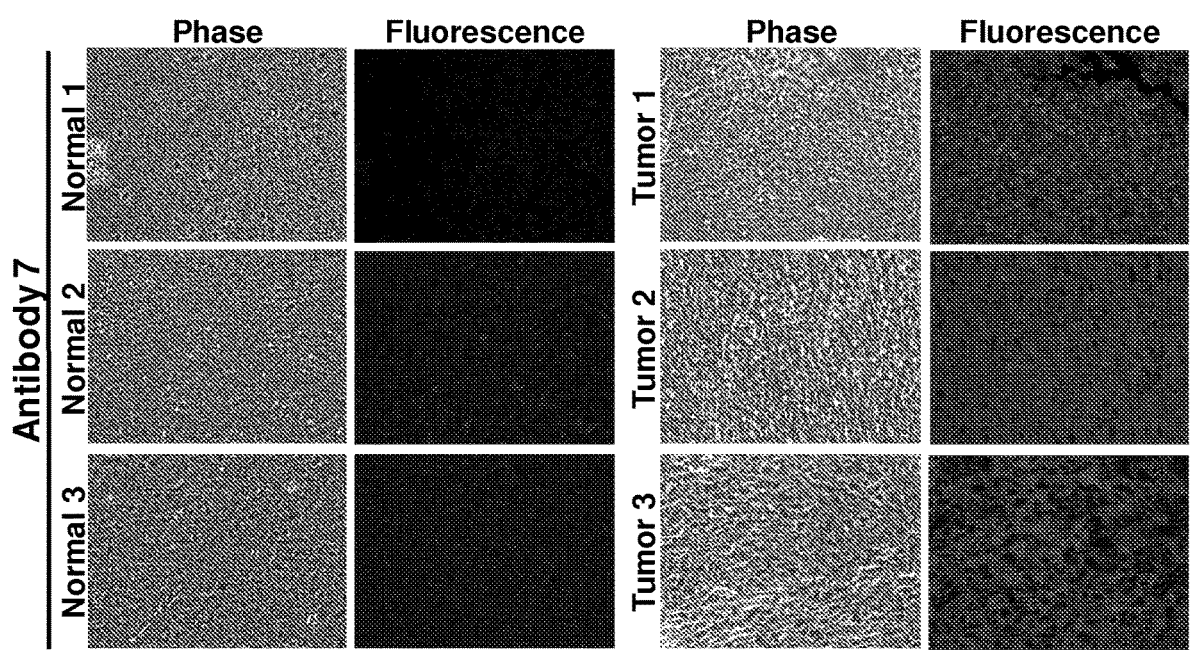

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

The terms "antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a polypeptide to a specific binding partner when an excess of antibody reduces the quantity of the polypeptide bound to the specific binding partner by at least about 20%, 40%, 60% or 80%, and more usually greater than about 85% (as measured in an in vitro competitive binding assay).

The term "monoclonal" refers to an antibody that specifically binds to a sequence of amino acid and/or a specific epitope of an antigen.

The term "polyclonal" refers to a combination of antibodies that recognize multiple epitope sites on a single antigen.

The term "epitope" includes any protein determinant capable of specific binding to an immunoglobulin. Epitope determinants usually consist of chemically active surface groupings of molecules such as amino acids or sugar side chains and usually have specific three-dimensional structural characteristics, as well as specific charge characteristics.

The term "agent" is used herein to denote a chemical compound, a mixture of chemical compounds, a biological macromolecule, or an extract made from biological materials.

The terms "patient", "subject", "mammalian host," and the like are used interchangeably herein, and refer to mammals, including human and veterinary subjects.

The terms "peptide(s)", "protein(s)" and "polypeptide(s)" are used interchangeably herein. "Polypeptide" refers to any peptide or protein comprising two or more amino acids joined to each other by peptide bonds or modified peptide bonds (i.e., peptide isomers). "Polypeptide(s)" refers to both short chains, commonly referred as peptides, oligopeptides or oligomers, and to longer chains generally referred to as proteins.

The terms "polynucleotide sequence" and "nucleotide sequence" are also used interchangeably herein.

The term "recombinant," refers to a protein is derived from a prokaryotic or eukaryotic expression system.

The term "wild type" refers to the naturally occurring polynucleotide sequence encoding a protein, or a portion thereof, or protein sequence, or portion thereof, respectively, as it normally exists in vivo.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

The term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "gene" or "recombinant gene" refers to a nucleic acid comprising an open reading frame encoding a polypeptide, including both exon and (optionally) intron sequences.

The terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The terms "chimeric protein" or "fusion protein" refer to a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

The term "isolated" as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

The phrases "parenteral administration" and "administered parenterally" refer to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, agent or other material other than directly into a specific tissue, organ, or region of the subject being treated (e.g., brain), such that it enters the animal's system and, thus, is subject to metabolism and other like processes, for example, subcutaneous administration.

This disclosure describes compositions and methods of treating a subject with cancer. The cancer includes cancer cells that express an immunoglobulin (Ig) superfamily cell adhesion molecule, such as a receptor protein tyrosine phosphatase (RPTP), that is proteolytically cleaved to produce extracellular fragments, which can modify or alter the cancer cell microenvironment to promote cancer cell survival, proliferation, and migration.

Ig superfamily CAMs, such as RPTP type IIb (e.g., PTPµ) and/or RPTP type IIa, are expressed by at least some cancer cells and endothelial cells, which support cell adhesion, as a transmembrane protein. RPTP type III) CAMs can include an extracellular segment that engages in homophilic binding. The extracellular segment can include a MAM domain, an immunoglobulin (Ig) domain and four-fibronectin type III (FNIII) repeats (FIG. 1A).

An example of RPTP type III) CAMs that binds homophilically and can mediate cell-cell aggregation is PTPµ. By binding homophilically it is meant that the "ligand" for PTPµ can have substantially the same amino acid sequence as the amino acid sequence of the PTPµ molecule on an adjacent cell. The Ig domain of PTPµ is responsible for promoting homophilic interactions and proper cell surface localization. The MAM domain also plays an important role in cell adhesion and sorting. The first two FNIII repeats contribute to efficient cell adhesion. When expressed on the cell surface, PTPµ mediates cell-cell adhesion and transduces signals in response to adhesion that may regulate contact inhibition of growth and/or movement.

In at least some human cancer cells and endothelial cells, which support cancer cell survival, the Ig superfamily CAMs that are expressed can be proteolytically cleaved to form an extracellular fragment, which is found to associate with or localize to the cancer cell microenvironment, and a membrane-free cytoplasmic fragment. For example, The extracellular fragment of PTPµ, which is expressed by cancer cells, such as glioblastoma (GBM) cells, lung cancer cells, breast cancer cells, prostate cancer cells, and/or melanoma cells can include, for example, a MAM domain, an immunoglobulin (Ig) domain and some of the fibronectin type III (FNIII) repeats. The scissors in FIG. 1A illustrates schematically one potential site in the FNIII domain where PTPµ can be cleaved to generate a 55 kDa N-terminal fragment. It will be appreciated that that PTPµ can be cleaved at other sites in the FNIII domain.

The cleaved extracellular fragment no longer includes the transmembrane domain and therefore contains adhesive domains that are no longer integral transmembrane adhesion molecules. These adhesive extracellular fragments can still serve as ligands for other cells or substrates for cell migration.

The proteolytically cleaved extracellular fragment can disrupt cancer cell adhesion function and induce signals that promote cancer cell survival, proliferation, and/or migration. It was found that agents or therapeutic agents that target and inhibit the cell adhesion function of the cleaved extracellular fragment or its receptor can inhibit and/or reduce cancer cell survival, proliferation, and migration.

Embodiments described herein therefore relate to methods of treating cancer in a subject by administering to the subject an agent that that specifically binds to or complexes with the proteolytically cleaved extracellular fragment of an Ig superfamily CAM or its receptor that is expressed by a cancer cell or another cell in the cancer cell microenvironment. The agent can inhibit cell adhesion function of the cleaved extracellular fragment or its receptor as well as inhibit and/or reduce cancer cell survival, proliferation, and migration. The cell adhesion function can include heterophilic or homophilic binding of the extracellular fragment or its receptor and the agent can inhibit binding of the extracellular fragment to its receptor.

In some embodiments, the Ig superfamily CAM that is expressed by the cancer cell or another cell in the cancer cell microenvironment can be an RPTP. The RPTP can be a RPTP type IIb or RPTP type IIa. In one example, the RPTP can include PTPs of the type IIb subfamily, such as PTPµ, PTPK, PTPρ, and PCP-2 (also called PTPλ). PTPµ-like RPTPs include a MAM (Meprin/A5-protein/PTPµ) domain, an Ig domain, and FNIII repeats. PTPµ can have the amino acid sequence of SEQ ID NO: 1, which is identified by Genbank Accession No. AAI51843.1. It will be appreciated that the PTPµ gene can generate splice variants such that the amino acid sequence of PTPµ can differ from SEQ ID NO: 1. In some embodiments, PTPµ can have an amino acid sequence identified by Genbank Accession No. AAH51651.1 and Genbank Accession No. AAH40543.1.

In certain embodiments, the cancer cell that expresses the proteolytically cleaved extracellular fragment of an Ig superfamily CAM can be a migratory, dispersive, invasive or metastatic cancer cell in a subject, and the agent can inhibit migration, dispersal, invasion or metastasis of the cancer. For example, the cancer cell can include at least one of a glioma, lung cancer, melanoma, or prostate cancer cell. Still other examples of cancer cells that express an RPTP, which can be proteolytically cleaved to produce extracellular fragments can be readily screened using, for example, immunoassays.

The proteolytically cleaved extracellular fragment of an Ig superfamily CAM can also be expressed by other cells in the cancer cell microenvironment. These other cells can include, for example, endothelial cells, stem cells, stromal cells, and immune cells that support cancer cell proliferation, migration, and survival.

The agent (or therapeutic agent) that specifically binds to or complexes with a proteolytically cleaved extracellular fragment of an immunoglobulin (Ig) superfamily CAM or its receptor that is expressed by a cancer cell or another cell in the cancer cell microenvironment can include any composition or substance that decreases and/or suppresses the cell adhesion function of the proteolytically cleaved extracellular fragment. The agent can include a targeting small molecule, polypeptide, antibody, and/or a fragment of an antibody, such as an Fc fused to the extracellular segment of an Ig superfamily CAM (Fc chimera), that binds to and/or complexes with the proteolytically cleaved extracellular fragment of the Ig superfamily CAM or its receptor that is expressed by a cancer cell or another cell in the cancer cell microenvironment and that can readily be administered to the subject using, for example, parenteral or systemic administration techniques (e.g., intravenous infusion).

In one aspect, the agent can include a polypeptide that binds to and/or complexes with the proteolytically cleaved extracellular fragment of the Ig superfamily CAM or its receptor that is expressed by a cancer cell or another cell in the cancer cell microenvironment. The polypeptide can have an amino acid sequence that is substantially homologous to consecutive amino acids (e.g., about 10 to about 50 consecutive amino acids) of a homophilic binding portion or domain of the proteolytically cleaved extracellular fragment of the Ig superfamily CAM or its receptor that is expressed by a cancer cell or another cell in the cancer cell microenvironment. By substantially homologous, it is meant the polypeptide has at least about 80%, about 90%, about 95%, about 96%, about 97%, about 98%, about 99% or about 100% sequence identity with a portion of the amino acid sequence (e.g., about 10 to about 50 consecutive amino acids) of the binding portion of the proteolytically cleaved extracellular fragment of the Ig superfamily cell adhesion molecule.

In one example, the homophilic binding portion of the Ig superfamily CAM can include, for example, the Ig domain of the cell adhesion molecule. In another example, where the Ig superfamily CAM is PTPµ, and the homophilic binding portion can include the Ig binding domain and the MAM domain.

In some embodiments, the polypeptide can have an amino acid sequence that is substantially homologous to about 10 to about 50 consecutive amino acids of a homophilic binding portion or domain of the proteolytically cleaved extracellular fragment of the Ig superfamily CAM or its receptor that is expressed by a cancer cell or another cell in the cancer cell microenvironment. In other embodiments, the polypeptide can have an amino acid sequence that is substantially homologous to about 10 to about 50 consecutive amino acids of the Ig binding domain and/or MAM domain of PTPµ (e.g., SEQ ID NO: 1) and readily crosses the blood brain barrier when systemically administered to a subject.

The development of a polypeptide that can target PTPµ is based on a large body of structural and functional data. The sites required for PTPµ-mediated homophilic adhesion have been well characterized. In addition, the crystal structure of PTPµ can provide information regarding which regions of each functional domain are likely to be exposed to the outside environment and therefore available for homophilic binding and targeting with the polypeptide.

In some embodiments, as illustrated schematically in FIG. 1, the proteolytically cleaved extracellular fragment of PTPµ (e.g., SEQ ID NO: 1) can include an amino acid sequence of SEQ ID NO: 2, the Ig, MAM, and FNIII binding region can comprise the amino acid sequence of SEQ ID NO: 3, and the polypeptide can have an amino acid sequence that is substantially homologous to about 10 to about 50 consecutive amino acids of SEQ ID NO: 2 or SEQ ID NO: 3. Examples of polypeptides that can specifically bind SEQ ID NO: 2 or SEQ ID NO: 3 and have an amino acid sequence that is substantially homologous to about 10 to about 50 consecutive amino acids of SEQ ID NO: 2 or SEQ ID NO: 3 are polypeptides that comprising an amino acid sequence selected from the group consisting of SEQ ID NO: 4, SEQ ID NO: 5, SEQ ID NO: 6, SEQ ID NO: 7, SEQ ID NO: 11, and SEQ ID NO: 12. Polypeptides comprising SEQ ID NO: 4, 5, 6, or 7 can recognize or bind to the MAM, Ig domain, or the FNIII repeats.

In other embodiments, a polypeptide that binds to and/or complexes with the proteolytically cleaved extracellular fragment of the Ig superfamily CAM or its receptor that is expressed by a cancer cell or another cell in the cancer cell microenvironment can have an amino acid sequence of SEQ ID NO: 8. SEQ ID NO: 8 is substantially homologous to SEQ ID NO: 2 and SEQ ID NO: 1 and can specifically bind to SEQ ID NO: 2 or SEQ ID NO: 3.

The therapeutic polypeptides described herein can be subject to various changes, substitutions, insertions, and deletions where such changes provide for certain advantages in its use. In this regard, therapeutic polypeptides that bind to and/or complex with a proteolytically cleaved extracellular portion of an Ig superfamily CAM or its receptor can correspond to or be substantially homologous with, rather than be identical to, the sequence of a recited polypeptide where one or more changes are made and it retains the ability to function as specifically binding to and/or complexing with the proteolytically cleaved extracellular portion of an Ig superfamily CAM.

The therapeutic polypeptide can be in any of a variety of forms of polypeptide derivatives and include, for example, amides, conjugates with proteins, cyclized polypeptides, polymerized polypeptides, analogs, fragments, chemically modified polypeptides, and the like derivatives.

The term "analog" includes any polypeptide having an amino acid residue sequence substantially identical to a sequence specifically shown herein in which one or more residues have been conservatively substituted with a functionally similar residue and that specifically binds to and/or complexes with the proteolytically cleaved extracellular portion of an Ig superfamily CAM as described herein. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue, such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

Additional residues may also be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. For example, the polypeptide having SEQ ID NO: 11 includes the polypeptide having SEQ ID NO: 5 with the addition of a glycine residue, and the polypeptide having SEQ ID NO: 12 includes the polypeptide having SEQ ID NO: 5 with the addition of cysteine and glycine residues. In addition, a subject polypeptide can differ by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 3, 4, 5, 6, 7, 8, 9, 10, 11, and 12.

In some cases, a peptide linker comprises two or more of the following amino acids: glycine, serine, alanine, and threonine.

Any polypeptide or compound may also be used in the form of a pharmaceutically acceptable salt. Acids, which are capable of forming salts with the polypeptides, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the polypeptides include inorganic bases such as sodium hydroxide, ammonium hydroxide, potassium hydroxide and the like; and organic bases such as mono-, di- and tri-alkyl and arylamines (e.g., triethylamine, diisopropylamine, methylamine, dimethylamine and the like) and optionally substituted ethanolamines (e.g., ethanolamine, diethanolamine and the like).

The therapeutic polypeptides can be synthesized by any of the techniques that are known to those skilled in the polypeptide art, including recombinant DNA techniques. Synthetic chemistry techniques, such as a solid-phase Merrifield-type synthesis, can be used for reasons of purity, antigenic specificity, freedom from undesired side products, ease of production, and the like. A summary of the many techniques available can be found in, for example: Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

It will be appreciated that the therapeutic polypeptides can bind to and/or complex with homophilic binding domains of proteolytically cleaved extracellular fragments of other Ig superfamily cell adhesion molecules, besides RPTPs. For example, a similar molecular detection strategy described herein can be used with any other Ig superfamily CAM having a homophilic binding cell surface protein whose ligand binding site is known. A large variety of cell surface proteins, including other phosphatases, are cleaved at the cell surface (See, for example, Streuli M, Saito H (1992) Expression of the receptor-linked protein tyrosine phosphatase LAR: proteolytic cleavage and shedding of the CAM-like extracellular region. EMBO J 11:897-907; Anders L, Ullrich A (2006) Furin-, ADAM 10-, and gamma-secretase-mediated cleavage of a receptor tyrosine phosphatase and regulation of beta-catenin's transcriptional activity. Mol Cell Biol 26:3917-3934; Haapasalo A, Kovacs DM (2007) Presenilin/gamma-secretase-mediated cleavage regulates association of leukocyte-common antigen-related (LAR) receptor tyrosine phosphatase with beta-catenin. J Biol Chem 282:9063-9072; Chow J P, Noda M (2008) Plasmin-mediated processing of protein tyrosine phosphatase receptor type Z in the mouse brain. Neurosci Lett 442:208-212; Craig S E, Brady-Kalnay S M. Tumor-derived extracellular fragments of receptor protein tyrosine phosphatases (RPTPs) as cancer molecular diagnostic tools. Anticancer Agents Med Chem. 2011 Jan. 11(1):133-40. Review; Craig S E, Brady-Kalnay S M. Cancer cells cut homophilic cell adhesion molecules and run. Cancer Res. 2011 Jan. 15; 71(2):303-9; Phillips-Mason P J, Craig S E, Brady-Kalnay S M. Should I stay or should I go? Shedding of RPTPs in cancer cells switches signals from stabilizing cell-cell adhesion to driving cell migration. Cell Adh Migr. 2011 Jul. 1; 5(4):298-305). These proteins represent additional targets for that can be readily used by the skilled artisan for forming therapeutic polypeptides that can be used to treat cancers (Barr A J, Ugochukwu E, Lee W H, King O N, Filippakopoulos P, Alfano I, Savitsky P, Burgess-Brown N A, Muller S, Knapp S (2009) Large-scale structural analysis of the classical human protein tyrosine phosphatome. Cell 136:352-363). Furthermore, the therapeutic polypeptides can be used as a starting point to develop higher affinity small molecules, antibodies, and/or antibody fragments with similar ligand binding capabilities. The development and screening of small molecules from pharmacophores of the polypeptides using, for example, in silico screening, can be readily performed, and the binding affinity of such identified molecules can be readily screened against targeting peptides using assays described herein to select small molecule agents.

In other embodiments, the therapeutic agent that specifically binds to or complexes with a proteolytically cleaved extracellular fragment of an Ig superfamily CAM or its receptor that is expressed by a cancer cell or another cell in the cancer cell microenvironment can be an antibody, such as a monoclonal antibody, a polyclonal antibody, or a humanized antibody. The antibody can include Fc fragments, Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

The antibody may be an antibody that has a single heavy chain variable region and no light chain sequence. Such an antibody, called a single domain antibody (sdAb) or a nanobody, has been reported to maintain the ability to bind to an antigen (Muyldemans S. et al., Protein Eng. (1994), 7 (9), 1129-35; and Hamers-Casterman C. et al., Nature (1993), 363 (6429), 446-8). These antibodies are also encompassed in the meaning of the functional fragment of the antibody as described herein.

In some embodiments, the antibody or fragment thereof can specifically or selectively bind to either the full length protein or a proteolytically cleaved extracellular fragment of PTPµ having the amino acid sequence of SEQ ID NO: 2. In other embodiments, the antibody or fragment thereof can specifically bind to the Ig and MAM binding region having the amino acid sequence of SEQ ID NO: 3 of the proteolytically cleaved extracellular fragment of PTPµ. In still other embodiments, the antibody or fragment thereof can specifically bind to an amino acid sequence selected from the group consisting of SEQ ID NO: 4, SEQ ID NO: 5, SEQ ID NO: 6, SEQ ID NO: 7, and SEQ ID NO: 8 of the proteolytically cleaved extracellular fragment of PTPµ.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. (See, for example, Kuby, Janis, Immunology, Third Edition, pp. 131-139, W.H. Freeman & Co. (1997), for a general overview of monoclonal antibody production, that portion of which is incorporated herein by reference).

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate an antibody or fragment thereof specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

In some embodiments, the therapeutic agent can include a polypeptide-Fc chimera that can specifically bind to the extracellular fragment or its receptor. Advantageously, in addition to its inhibition of cell adhesion function, the polypeptide-Fc chimera can induce immune responses, such as complement-dependent lysis and antibody-dependent cellular cytotoxicity that target tumor cells thereby eliciting anti-tumor activities. Moreover, the Fc region of the Fc chimera provides a binding site for other antibodies and can promote clustering, complexing, or aggregation of multiple antibodies, which can enhance the effectiveness of the polypeptide-Fc chimera in binding to and/or complexing with the proteolytically cleaved extracellular fragment of the Ig superfamily CAM or its receptor that is expressed by a cancer cell or another cell in the cancer cell microenvironment Chimeric proteins that can combine the Fc regions of IgG with one or more domains of another protein, such as various cytokines and soluble receptors, are known. These chimeric proteins can be fusions of human Fc regions and human domains of another protein. These chimeric proteins would then be a "humanized Fc chimera", which would be advantageous as a human therapeutic. (See, for example, Capon et al., Nature, 337:525-531, 1989; Chamow et al., Trends Biotechnol., 14:52-60, (1996); U.S. Pat. Nos. 5,116, 964 and 5,541,087). The chimeric protein can be a homodimeric protein linked through cysteine residues in the hinge region of IgG Fc, resulting in a molecule similar to an IgG molecule without the $C_{H1}$ domains and light chains. Due to the structural homology, such Fc fusion proteins exhibit in vivo pharmacokinetic profile comparable to that of human IgG with a similar isotype. This approach has been applied to several therapeutically important cytokines, such as IL-2 and IFN-α, and soluble receptors, such as TNF-Rc and IL-5-Rc (See, for example, U.S. Pat. Nos. 5,349,053, 6,224,867 and 7,250,493).

In some embodiments, the polypeptide-Fc chimera is a chimeric molecule that includes a human sequence encoded polypeptide fused to a human Fc fragment and is capable of binding to or complexing with a proteolytically cleaved extracellular fragment of an Ig superfamily CAM or its receptor that is expressed by a cancer cell or another cell in the cancer cell microenvironment.

The polypeptide portion of the polypeptide-Fc chimera used for methods described herein may be a polypeptide having an amino acid sequence that is substantially homologous to about 10 to about 50 consecutive amino acids of the Ig binding domain and/or MAM domain of PTPµ (e.g., SEQ ID NO: 1) and readily cross the blood brain bather when systemically administered to a subject. In some embodiments, the polypeptide can have an amino acid sequence that is substantially homologous to about 10 to about 50 consecutive amino acids of SEQ ID NO: 2 or SEQ ID NO: 3. Examples of polypeptides that can specifically bind SEQ ID NO: 2 or SEQ ID NO: 3 and have an amino acid sequence that is substantially homologous to about 10 to about 50 consecutive amino acids of SEQ ID NO: 2 or SEQ ID NO: 3 are polypeptides having an amino acid sequence selected from the group consisting of SEQ ID NO: 4, SEQ ID NO: 5, SEQ ID NO: 6, and SEQ ID NO: 7. In other embodiments, the polypeptide portion of the polypeptide-Fc chimera used for methods described herein may be a polypeptide having an amino acid sequence of SEQ ID NO: 8.

The polypeptide portion of the polypeptide-Fc chimera, similar to the therapeutic polypeptide described above, can be subject to various changes, substitutions, insertions, and deletions where such changes provide for certain advantages in its use. In this regard, polypeptide portion correspond to or be substantially homologous with, rather than be identical to, the sequence of a recited polypeptide where one or more changes are made and it retains the ability to function as specifically binding to and/or complexing with the proteolytically cleaved extracellular portion of an Ig superfamily cell adhesion molecule.

The Fc portion of the polypeptide-Fc chimera is a domain that binds an activating Fc receptor, such as an activating Fc Ig domain and includes the hinge region that allows for dimerization. The Fc portion of the polypeptide-Fc chimera can be readily adapted to render it species-specific. For use in a murine system, e.g., cells derived from a mouse, the Fc fragment used to generate polypeptide-Fc can be that of a murine origin. In some embodiments, an Fc fragment of the murine $IgG_{2a}$ can be used.

For use in a human subject, e.g., for cancer treatment, the Fc fragment used to generate the polypeptide-Fc chimera is of a human origin. In some embodiments, the polypeptide-Fc chimera comprises an activating Fc Ig domain. Among the four human IgG isotypes, an activating Fc domain of $IgG_1$ can be used for the preparation of the polypeptide-Fc chimera. In certain embodiments, the Fc portion can have an amino acid sequence of SEQ ID NO: 9.

It is appreciated that different antibody isotypes have a varying degree of cytotoxic potential in vivo (See, for example, Nimmerjahn F. & Ravetch J V., 2006, Immunity, 24:19-28). For example, the murine $IgG_{2a}$ and $IgG_{2b}$ isotypes are more efficient in clearing infections, such as bacterial infections and viral infections and in killing tumor cells than their $IgG_1$ or $IgG_3$ counterparts. This is attributable at least in part to differential ratios of activating versus inhibitory FcRs present in vivo. Similarly, with respect to human IgG isotypes, $IgG_1$ and $IgG_3$ have a stronger interaction with FcRs than $IgG_2$ or $IgG_4$. Moreover, certain polymorphic allotypes of a given isotype may influence affinity for an Fc receptor. Indeed, there are allelic variants of activating FcRs that will significantly affect the affinity for certain antibody isotypes. For example, the FcγRIIIa receptor 158V allotype displays a higher affinity for human immunoglobulin $G_1$ and increased antibody-dependent cellular cytotoxicity (Cartron G. et al., 2002, Blood, 99: 754-758).

Thus, as shall be clear to the skilled artisan, it is possible to optimize the interaction between the Fc portion of the polypeptide-Fc chimera to its corresponding Fc receptor by strategically selecting or modifying the Fc allele used for preparing the polypeptide-Fc chimera. Accordingly, a mutant or an allotype of an Fc fragment can be used here for the polypeptide-Fc chimera described herein. A number of useful mutations within an Fc domain have been described, which can affect the interaction of an Fc and its receptor, the effector function of the Fc, as well as the half-life of the Fc-containing molecule. These include specific amino acid substitutions and/or modifications to carbohydrate moieties in the Fc. (For review, see, for example, Liu et al., 2008, Immunological Reviews, 222:9-27; Nimmerjahn & Ravetch, 2007, Curr. Opin. Immunol., 19(2): 239-45).

In other embodiments, the polypeptide-Fc chimera can be engineered with an enhanced complement activity. Generally, complement can be activated by at least three pathways, leading to the formation of the membrane attack complex (MAC) C5b-9, which forms pores in the plasma membranes of target cells and causes their lysis. Clq binding to the Fc domain is a critical step in this process. Among the human IgG subclasses, only $IgG_1$ and $IgG_3$ can initiate the complement cascade. In some embodiments, mutations are introduced to the Fc domain of the polypeptide-Fc chimera, so as to promote Clq recruitment and the Clq-Fc interaction. The residues of the Fc targeted for such mutations include, but are not limited to: Asp270, Lys322, Pro329 and Pro331. These mutations involve substituting the corresponding residue(s) with nonpolar neutral amino acids, such as Ala, Met, or Trp. In a specific embodiment, the polypeptide-Fc contains the mutation, Lys326Trp, Glu333Ser or both.

In addition, it should be noted that when chimeric or fusion proteins with artificial sequences and activities are used as therapeutic agents, in some circumstances, patients treated with such a chimeric or fusion protein trigger an unwanted immune response, such as development of antibodies against the agent. Certain structural modifications of an Fc fragment have been shown to reduce immunogenicity of a therapeutic fusion protein. See, for example, U.S. Pat. No. 6,992,174 B2, which is incorporated by reference herein; Liu et al., 2008, Immunological Reviews, 222:9-27. Such modifications may be useful for an effective design of the polypeptide-Fc chimera described herein.

The polypeptide-Fc chimera used in the methods may include a linking moiety that connects the polypeptide portion with an Fc fragment. In some cases, a hinge region of Fc fusion protein molecules serves as a spacer between the Fc region and the fused polypeptide (e.g., soluble receptor), allowing these two parts of the molecule to function separately.

In some embodiments, the Fc portion and the polypeptide portion that comprise a chimeric molecule are linked via a linking molecule which is not a contiguous portion of either the polypeptide or Fc portions and which covalently joins an amino acid of the polypeptide to an amino acid of Fc. As used herein, a linking molecule that is "not a contiguous portion" means that the polypeptide portion and the Fc portion of the chimera are connected via an additional element that is not a part of the polypeptide or immunoglobulin that is contiguous in nature with either of the chimeric portions and functions as a linker.

In some embodiments, the linking molecule may be a peptide linker. Where the linker is a peptide linker, the polypeptide-Fc chimera may be produced as a single recombinant polypeptide using a conventional molecular biological/recombinant DNA method.

In other embodiments, a flexible peptide linker can be used. A flexible peptide linker can be about 20 or fewer amino acids in length. For example, a peptide linker can contain about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

Alternatively, a linking molecule may be a non-peptide linker. As used herein, a non-peptide linker useful for the method described herein is a biocompatible polymer including two or more repeating units linked to each other. Examples of the non-peptide polymer include but are not limited to: polyethylene glycol (PEG), polypropylene glycol (PPG), co-poly(ethylene/propylene)glycol, polyoxyethylene (POE), polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, and heparin. For more detailed descriptions of non-peptide linkers useful for Fc fusion molecules, see, for example, WO/2006/107124, which is incorporated by reference herein. Typically such linkers will have a range of molecular weight of about 1 kDa to 50 kDa, depending upon a particular linker. For example, a typical PEG has a molecular weight of about 1 to 5 kDa, and polyethylene glycol has a molecular weight of about 5 kDa to 50 kDa, and more preferably about 10 kDa to 40 kDa.

Molecular biological and biochemical techniques for preparing an Fc chimera are known. In some embodiments, the polypeptide-Fc chimera can be produced by conventional recombinatory DNA methods. In other embodiments, the polypeptide-Fc chimera can be produced as a single (e.g., contiguous) recombinant polypeptide. In still other embodiments, two or more portions of the polypeptide-Fc can be produced as separate fragments and are subsequently linked together to yield the polypeptide-Fc chimera. For example, the polypeptide portion of the polypeptide-Fc chimera and an Fc portion of the polypeptide-Fc chimera can each be produced as separate recombinant polypeptides then fused together by a chemical linking means to yield the polypeptide-Fc. This production methodology may be preferred particularly in situations where a non-peptide linking molecule is employed. Similarly, this production methodology may be also preferred if a chimeric polypeptide-Fc does not fold correctly (e.g., does not properly bind a ligand) when made as a single contiguous polypeptide.

For the production of recombinant polypeptides, a variety of host organisms may be used. Examples of hosts include, but are not limited to: bacteria, such as E. coli, yeast cells, insect cells, plant cells and mammalian cells. Choice of a host organism will depend on the particular application of the polypeptide-Fc chimera. The skilled artisan will understand how to take into consideration certain criteria in selecting a suitable host for producing the recombinant polypeptide. Factors affecting selection of a host include, for example, post-translational modifications, such as phosphorylation and glycosylation patterns, as well as technical factors, such as the general expected yield and the ease of purification. Host-specific post-translational modifications of the polypeptide-Fc chimera, which is to be used in vivo, should be carefully considered because certain post-translational modifications are known to be highly immunogenic (antigenic).

In certain aspects, the therapeutic agent can be directly or indirectly labeled with a detectable moiety. The detectable moiety is to facilitate detection step of therapeutic agent allowing visualization of the complex formed by binding of the therapeutic agent to the proteolytically cleaved extracellular fragment of the Ig superfamily CAM. The detectable moiety can be selected such that it generates a signal, which can be measured and whose intensity is related (preferably proportional) to the amount of the molecular probe bound to the tissue being analyzed. Methods for labeling biological molecules, such as polypeptides and antibodies are well-known in the art.

Any of a wide variety of detectable moieties can be used with the therapeutic agents described herein. Examples of detectable moieties include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In one example, the detectable moiety can include a radiolabel that is detected using gamma imaging wherein emitted gamma irradiation of the appropriate wavelength is detected. Methods of gamma imaging include, but are not limited to, SPECT and PET. For SPECT detection, the chosen radiolabel can lack a particular emission, but will produce a large number of photons in, for example, a 140-200 keV range. For PET detection, the radiolabel can be a positron-emitting moiety, such as $^{19}$F.

In another example, the detectable moiety can an include MRS/MRI radiolabel, such as gadolinium, $^{19}$F, $^{13}$C, that is coupled (e.g., attached or complexed) with the therapeutic agent using general organic chemistry techniques. The detectable moiety can also include radiolabels, such as $^{18}$F, $^{11}$C, $^{75}$Br, or $^{76}$Br for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. The detectable moiety can also include 123I for SPECT. The 123I can be coupled to the therapeutic agent can by any of several techniques known to the art. See, e.g., Kulkarni, Int. J. Rad. Appl. & Inst. (Part B) 18: 647 (1991), the contents of which are hereby incorporated by reference. In addition, detectable moiety can include any radioactive iodine isotope, such as, but not limited to $^{131}$I, $^{125}$I, or $^{123}$I. The radioactive iodine isotopes can be coupled to the therapeutic agent by iodination of a diazotized amino derivative directly via a diazonium iodide, see Greenbaum, F. Am. J. Pharm. 108: 17 (1936), or by conversion of the unstable diazotized amine to the stable triazene, or by conversion of a non-radioactive halogenated precursor to a stable tri-alkyl tin derivative which then can be converted to the iodo compound by several methods well known to the art.

The detectable moiety can further include known metal radiolabels, such as Technetium-99m ($^{99m}$Tc). Modification of the therapeutic agent to introduce ligands that bind such metal ions can be effected without undue experimentation by one of ordinary skill in the radiolabeling art. The metal radiolabeled molecular probes can then be used to detect cancers, such as GBM in the subject. Preparing radiolabeled derivatives of Tc99m is well known in the art. (See, for example, Zhuang et al., "Neutral and stereospecific Tc-99m complexes: [99mTc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997)).

In some embodiments, the therapeutic agent with the detectable moiety when used in the methods described herein can be detected upon administration to the subject to measure the efficacy of the therapeutic agent in treating cancer in the subject. For example, a therapeutically effective amount of an agent that specifically binds to or complexes with a proteolytically cleaved extracellular fragment of an Ig superfamily CAM or its receptor that is expressed by a cancer cell or another cell in the cancer cell microenvironment and that includes a detectable moiety can be administered to the subject to treat cancer. The therapeutic agent bound to and/or complexed with the proteolytically cleaved extracellular fragment of the Ig superfamily cell adhesion molecule can then detected in the subject to provide the location and/or distribution of cancer cells in the subject. The distribution of the therapeutic agent may be correlated with the presence or absence of cancer cells in a tissue of the subject. A distribution may be dispositive for the presence or absence of a cancer cells or may be combined with other factors and symptoms by one skilled in the art to positively detect the presence or absence of cancer cells, cancer metastases or define a tumor margin in the subject. The location and/or distribution of the cancer cells in the subject can be monitored over time by subsequent administrations of the therapeutic agent to determine efficacy of the therapeutic agent in treating the cancer. A reduction, for example, in cancer volume, growth, migration, and/or dispersal in a subject may be indicative of the efficacy of a given therapeutic agent. This can provide a direct clinical efficacy endpoint measure of the therapeutic.

In some embodiments, the therapeutic agents can be provided in a pharmaceutical composition. The pharmaceutical compositions can include a pharmaceutically effective amount of a therapeutic agents described above and a pharmaceutically acceptable diluent or carrier.

The term "pharmaceutically acceptable carrier", "diluents", "adjuvant" and "physiologically acceptable vehicle" and the like are to be understood as referring to an acceptable carrier or adjuvant that may be administered to a patient, together with an agent of this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

In addition, the term "pharmaceutically effective amount" or "therapeutically effective amount" refers to an amount (dose) effective in treating a patient, having, for example, cancer, such as glioblastoma multiforme. It is also to be understood herein that a "pharmaceutically effective amount" may be interpreted as an amount giving a desired therapeutic effect, either taken into one dose or in a dosage or route or taken alone or in combination with other therapeutic agents. A "pharmaceutically effective amount" may be understood as an amount of the therapeutic agent that is effective to that decreases and/or suppresses the cell adhesion function of the proteolytically cleaved extracellular fragment.

Determination of a therapeutically effective amount is within the capability of those skilled in the art. The exact formulation, route of administration and dosage can be chosen by the individual physician in view of the patient's condition.

Pharmaceutical compositions described herein can be administered in a suitable pharmaceutical carrier by one of several routes, which include direct injection, and topical application. Formulations of the compositions will vary according to the route of administration selected (e.g., solution or emulsion).

In some embodiments, the therapeutic agent can be conjugated onto a nanoparticle. An example of a nanoparticle polypeptide conjugate can include a nanoparticle conjugated to a therapeutic polypeptide, and a fluorophore (or gadolinium) imaging agent. Nanoparticles are a new class of drug carriers with precisely defined nanosize (2-5 nm). These carriers have compact molecular morphology and high surface functionalities for effective conjugation of therapeutic agents and imaging agents. In one example, the nanoparticle can have a size (e.g., about 3 nm) that allows effective transport and distribution of the targeted delivery systems in solid tumors.

The therapeutic agent can be conjugated to the surface of the nanoparticle via, for example, a PEG spacer (e.g., 1,000 Da) to a functional group pre-conjugated to the nanoparticle. The PEG spacer is designed to reduce the steric hindrance of the drug carrier and to achieve effective specific binding to the target. The therapeutic agent can also be conjugated to the nanoparticle via, for example, a disulfide spacer.

In some embodiments, the nanoparticle comprising the therapeutic peptide can be directly or indirectly labeled with a detectable moiety or imaging agent. The role of a detectable moiety is to facilitate the detection step of a nanoparticle by allowing visualization of the complex formed by binding of the therapeutic peptide to the proteolytically cleaved extracellular fragment of the RPTP of the cancer cell. The detectable moiety can be selected such that it generates a signal, which can be measured and whose intensity is related (preferably proportional) to the amount of the nanoparticle bound to the tissue being treated. Methods for labeling biological molecules, such as polypeptides and antibodies are well-known in the art (see for example, *Methods in Enzymol.*, 1974, Vol. 34, Academic Press: New York, N.Y.; and, *Anal. Biochem.*, 1988, 171: 1-32).

In one embodiment, the therapeutic agent described herein can be administered to a cancer cell, e.g., glioblastoma multiforme cell, prostate cancer, lung cancer, melanoma, or other cell of the cancer or tumor cell microenvironment, of a subject by contacting the cell of the subject with a pharmaceutical composition described above. In one aspect, a pharmaceutical composition can be administered directly to the cell by direct injection. Alternatively, the pharmaceutical composition can be administered to the subject systematically by parenteral administration, e.g., intravenous administration).

In a further example, the therapeutic agent can be used in combination and adjunctive therapies for inhibiting cancer cell proliferation, growth, and motility. The phrase "combination therapy" embraces the administration of a therapeutic agent, which specifically binds to or complexes with a proteolytically cleaved extracellular fragment of an Ig superfamily CAM or its receptor that is expressed by a cancer cell or another cell in the cancer cell microenvironment, and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). The phrase "adjunctive therapy" encompasses treatment of a subject with agents that reduce or avoid side effects associated with the combination therapy of this application.

A combination therapy is intended to embrace administration of these therapeutic agents in a sequential manner, that is, wherein different therapeutic agents are administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of therapeutic agents can be effected by an appropriate routes including, but not limited to, oral routes, intravenous routes, intramuscular routes, and direct absorption through mucous membrane tissues. The therapeutic agents can be administered by the same route or by different routes. The sequence in which the therapeutic agents are administered is not narrowly critical.

Combination therapy also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at a suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the therapeutic agent, which specifically binds to or complexes with a proteolytically cleaved extracellular fragment of an Ig superfamily CAM or its receptor that is expressed by a cancer cell or another cell in the cancer cell microenvironment, can be administered in combination at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Other embodiments described herein relating to a method of treating a subject having or suspected of having cancer can include first obtaining a sample or biopsy of cells and/or tissue having or suspected of having cancer cells from the subject. The biopsied cells and/or tissue is then assayed to determine if the biopsied cells and/or tissue includes cancer cells expressing an Ig superfamily cell adhesion molecule, such as PTPµ, which has been proteolytically cleaved to form a extracellular fragment.

In some embodiments, the sample or biopsy from the subject can be assayed by contacting the sample or biopsy with a molecular probe is detectable upon binding to the proteolytically cleaved extracellular fragment to provide the location and/or distribution of the cancer cells in the biopsied cells and/or tissue.

In one example, the molecular probe can include a targeting peptide that binds homophilically to a proteolytically cleaved extracellular fragment of the Ig superfamily cell adhesion molecule. For example, the targeting peptide can have an amino acid sequence that has an at least about 80%, at least about 85%, at least about 90%, at least about 95%, or at least about 99% sequence identity with about 10 to about 50 consecutive amino acids of SEQ ID NO: 3 and a detectable moiety that is linked to the targeting peptide and generates a signal to facilitate detection of the molecular probe bound homophilically to the proteolytically cleaved extracellular fragment in the subject.

In another example, the molecular probe can include an antibody, such as a monoclonal antibody, that specifically or selectively binds to a proteolytically cleaved extracellular fragment of the Ig superfamily cell adhesion molecule. Similar to a therapeutic antibody described herein, the antibody can include Fc fragments, Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

In some embodiments, the antibody can be a component of an immunoassay, which is used to detect the proteolytically cleaved extracellular fragment. In other embodiments, the antibody can include a detectable moiety that facilitates detection of the antibody bound to the proteolytically cleaved extracellular fragment in the sample or biopsy.

Detection of proteolytically cleaved extracellular fragments of the Ig superfamily CAM in the sample or biopsy is indicative that the subject has cancer cells expressing an Ig superfamily cell adhesion molecule, and that treatment of the subject with an amount of a therapeutic agent described herein that specifically binds to or complexes with a proteolytically cleaved extracellular fragment of an Ig superfamily CAM or its receptor can have efficacy or enhanced efficacy in inhibiting and/or reducing cancer cell survival, proliferation, and migration in the subject. In contrast, absence of proteolytically cleaved extracellular fragments of the Ig superfamily CAM in the sample or biopsy is indicative that the subject does not have cancer cells expressing an Ig superfamily CAM and that treatment of the subject with a therapeutically effective amount of a therapeutic agent described herein that specifically binds to or complexes with a proteolytically cleaved extracellular fragment of an Ig superfamily CAM or its receptor will have reduced efficacy or little if any efficacy in inhibiting and/or reducing cancer cell survival, proliferation, and migration in the subject.

A therapeutically effective amount of an agent described herein that specifically binds to or complexes with a proteolytically cleaved extracellular fragment of an immunoglobulin (Ig) superfamily cell adhesion molecule (CAM) or its receptor that is expressed by a cancer cell or another cell in the cancer cell microenvironment is then administered to the subject if the sample or biopsy if proteolytically cleaved extracellular fragments of the Ig superfamily CAM are detected in the sample or biopsy.

The following examples are included to demonstrate different embodiments of the invention. It should be appreciated by those of skill in the art that the techniques disclosed in the examples, which follow represent techniques discovered by the inventor to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

Example 1

In this Example, we tested the efficacy of the SBK2 peptide in treating primary human brain tumor xenografts. The studies were performed using an imaging dose of the SBK2 peptide probe in 3 sequential injections that were two days apart in a heterotopic GBM flank tumor model.

Peptide Synthesis and Conjugation

The SBK2 peptide with an additional glycine residue (GEGDDFNWEQVNTLTKPTSD (SEQ ID NO: 11)) and a scrambled sequence of the SBK2 peptide (GFTQPETGTDNDLWSVDNEK (SEQ ID NO: 10)) were synthesized using a standard Fmoc based solid phase strategy with an additional N-terminal glycine residue as previously described. Following synthesis, the N-terminal glycine residues of the SBK2 and scrambled probes were conjugated to Cy5 NHS ester dye (GE Healthcare Life Sciences, USA).

Heterotopic Xenograft Tumors

Human Gli36Δ5 glioblastoma cells constitutively overexpress the vIII mutant forms of the EGFR gene (Tyminski E, Leroy S, Terada K, Finkelstein D M, Hyatt J L, Danks M K, Potter P M, Saeki Y, Chiocca E A (2005) Brain tumor oncolysis with replication-conditional herpes simplex virus type 1 expressing the prodrug-activating genes, CYP2B1 and secreted human intestinal carboxylesterase, in combination with cyclophosphamide and irinotecan. Cancer Res 65:6850-6857). Human LN-229 glioblastoma cells were obtained from American Type Culture Collection, Manassas, Va. Gli36Δ5 or LN-229 cells were harvested for flank implantation by trypsinization. In some experiments, the cells were infected with lentivirus to express GFP (Tyagi M, Karn J (2007) CBF-1 promotes transcriptional silencing during the establishment of HIV-1 latency. EMBO J 26:4985-4995) 48 hours prior to harvesting. The cells ($2\times10^6$ cells for flank tumor implants) were re-suspended in a 1:1 dilution of PBS and Matrigel (BD Biosciences; Franklin Lakes, N.J. for a total volume of 250-300 μL per flank tumor implant per animal.

NIH athymic nude female mice (5-8 weeks and 20-25 g upon arrival, NCI-NIH) were obtained. All animal protocols were IACUC approved. For flank tumor implants, mice were anesthetized with inhaled isofluorane:oxygen for immobilization. The Matrigel: cell mixture was loaded into a 1 mL syringe fitted with a 26-gauge needle and kept on ice. The mixture was injected subcutaneously in the right flank region of the mouse.

$1.4\times10^6$ CNS-1 or LN-229 cells were implanted subcutaneously in the flank region of nude mice. At 7 days (CNS-1) or 14 days (LN-229) post-implantation, treatment with peptides began. SBK2 or Scrambled peptides were injected at a final dose of 2 nM per mouse (based on animal weight). CNS-1 tumors were treated every 2-3 days (every 4 days for LN-229), for 5 total treatments. 5-7 days after the final peptide treatment animals were sacrificed.

On each peptide treatment day, flank tumors were imaged using the Maestro FLEX In Vivo Imaging System. Images were acquired before and 20 minutes after peptide injection. Tumors were measured through the skin using calipers; length, width and height of the tumors were recorded on each treatment day. On the day the animals were sacrificed, tumors were measured before removal (through the skin) and after removal.

Results

FIGS. 2(A-B) illustrate (A) images heterotopic xenograft flank tumors of mice intravenously administered a scrambled control polypeptide or a therapeutic polypeptide, SBK2 (SEQ ID NO: 5), and (B) a graph showing the weight and volume of flank tumors of the mice intravenously administered the scrambled and control polypeptide. As shown in FIGS. 2(A-B), a 50% reduction in tumor volume and a 35% reduction in weight was observed only with the PTPμ specific SBK2 peptide.

Example 2

In this example, sections of noncancerous normal cortical brains tissue from epilepsy patients or GBM tumor were labeled with a series of anti-PTPμ antibodies to the proteolytically cleaved extracellular fragment of PTPμ (Antibodies 1-7) and visualized with Alexa Flour 568 secondary antibody to determine if GBM tumors in brain tissue of a subject could be detected and distinguished from normal tissue using the anti-PTPμ antibodies. Only a subset of the antibodies was able to recognize the PTPμ fragment in the GBM tumor tissue.

A polypeptide having the amino acid sequence of SEQ ID NO: 5 with an additional c-terminal cysteine residue was coupled to keyhole limpet hemocyanin and used to generate monoclonal toward the extracellular segment of PTPμ.

FIG. 3(A-D) illustrates images showing sections of non-cancerous normal cortical brain tissue from epilepsy patients or GBM tumors labeled with a series of anti-PTPμ antibodies to SEQ ID NO: 5 (Antibodies 1-7) and visualized with Alexa Flour 568 secondary antibody. As shown in FIG. 3(A-D), Antibody 7 was found to readily distinguish normal cortical brain tissue from GBM tumors and therefore can be used in an assay for identifying subjects with cancer cells expressing PTPμ or in methods of treating a subject with cancer cells expressing PTPμ described herein.

From the above description, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of treating cancer in a subject, comprising: administering to the subject a therapeutically effective amount of a polypeptide-Fc chimera that specifically binds to or complexes with a proteolytically cleaved extracellular fragment of a receptor protein tyrosine phosphatase (RPTP) or its receptor that is expressed by a cancer cell or another cell in the cancer cell microenvironment, wherein the polypeptide-Fc is consist of a polypeptide and an Fc, and wherein the polypeptide is of the polypeptide-Fc chimera is consists of an amino acid sequence selected from the group consisting of SEQ ID NO: 4, SEQ ID NO: 5, SEQ ID NO: 6, SEQ ID NO: 7, SEQ ID NO: 8, SEQ ID NO: 11, and SEQ ID NO: 12, and wherein the therapeutically effective amount of polypeptide-Fc chimera administered is an amount effective to inhibit cancer cell survival, proliferation, and migration.

2. The method of claim 1, wherein the cell adhesion function comprises heterophilic or homophilic binding of the extracellular fragment or its receptor.

3. The method of claim 1, wherein the RPTP molecule is PTPμ.

4. The method of claim 1, wherein the cancer cell being one or more of, a migratory, dispersive, invasive and metastatic cancer cell in a subject and the agent inhibiting migration, dispersal, invasion or metastasis of the cancer.

5. The method of claim 1, wherein the cancer cell comprising at least one of a glioma, lung cancer, melanoma, or prostate cancer cell.

6. The method of claim 1, wherein the another cell in the cancer cell microenvironment comprising a stem cell, endothelial cell, stromal cell or immune cell that supports survival of the cancer cell.

7. The method of claim 1, wherein the extracellular fragment comprising amino acid sequence of SEQ ID NO: 2.

8. The method of claim 1, wherein the agent specifically binding to an extracellular fragment having an amino acid sequence of SEQ ID NO: 2.

9. The method of claim 1, wherein the polypeptide of the polypeptide-Fc chimera specifically binding to an amino acid sequence of SEQ ID NO: 2.

10. The method of claim 1, wherein the Fc portion of the polypeptide-Fc chimera comprising the amino acid sequence of SEQ ID NO: 9.

11. The method of claim 1, further comprising treating the subject with a combination cancer therapy, wherein the combination cancer therapy comprises an immunotherapy, a radiation therapy, or a chemotherapy.

* * * * *

SEQUENCE LISTING

```
<160> NUMBER OF SEQ ID NOS: 12

<210> SEQ ID NO 1
<211> LENGTH: 1465
<212> TYPE: PRT
<213> ORGANISM: Homo sapiens

<400> SEQUENCE: 1

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
            100                 105                 110

Leu Leu Asn Val Tyr Val Lys Val Asn Asn Gly Pro Leu Gly Asn Pro
        115                 120                 125

Ile Trp Asn Ile Ser Gly Asp Pro Thr Arg Thr Trp Asn Arg Ala Glu
    130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
    210                 215                 220

Val Arg Asp Ala Pro Leu Lys Glu Ile Lys Val Thr Ser Ser Arg Arg
225                 230                 235                 240
```

-continued

```
Phe Ile Ala Ser Phe Asn Val Val Asn Thr Thr Lys Arg Asp Ala Gly
                245                 250                 255
Lys Tyr Arg Cys Met Ile Arg Thr Glu Gly Val Gly Ile Ser Asn
            260                 265                 270
Tyr Ala Glu Leu Val Val Lys Glu Pro Pro Val Pro Ile Ala Pro Pro
            275                 280                 285
Gln Leu Ala Ser Val Gly Ala Thr Tyr Leu Trp Ile Gln Leu Asn Ala
        290                 295                 300
Asn Ser Ile Asn Gly Asp Gly Pro Ile Val Ala Arg Glu Val Glu Tyr
305                 310                 315                 320
Cys Thr Ala Ser Gly Ser Trp Asn Asp Arg Gln Pro Val Asp Ser Thr
                325                 330                 335
Ser Tyr Lys Ile Gly His Leu Asp Pro Asp Thr Glu Tyr Glu Ile Ser
            340                 345                 350
Val Leu Leu Thr Arg Pro Gly Glu Gly Gly Thr Gly Ser Pro Gly Pro
        355                 360                 365
Ala Leu Arg Thr Arg Thr Lys Cys Ala Asp Pro Met Arg Gly Pro Arg
    370                 375                 380
Lys Leu Glu Val Val Glu Val Lys Ser Arg Gln Ile Thr Ile Arg Trp
385                 390                 395                 400
Glu Pro Phe Gly Tyr Asn Val Thr Arg Cys His Ser Tyr Asn Leu Thr
                405                 410                 415
Val His Tyr Cys Tyr Gln Val Gly Gly Gln Gln Val Arg Glu Glu
            420                 425                 430
Val Ser Trp Asp Thr Glu Asn Ser His Pro Gln His Thr Ile Thr Asn
        435                 440                 445
Leu Ser Pro Tyr Thr Asn Val Ser Val Lys Leu Ile Leu Met Asn Pro
    450                 455                 460
Glu Gly Arg Lys Glu Ser Gln Glu Leu Ile Val Gln Thr Asp Glu Asp
465                 470                 475                 480
Leu Pro Gly Ala Val Pro Thr Glu Ser Ile Gln Gly Ser Thr Phe Glu
                485                 490                 495
Glu Lys Ile Phe Leu Gln Trp Arg Glu Pro Thr Gln Thr Tyr Gly Val
            500                 505                 510
Ile Thr Leu Tyr Glu Ile Thr Tyr Lys Ala Val Ser Ser Phe Asp Pro
        515                 520                 525
Glu Ile Asp Leu Ser Asn Gln Ser Gly Arg Val Ser Lys Leu Gly Asn
    530                 535                 540
Glu Thr His Phe Leu Phe Phe Gly Leu Tyr Pro Gly Thr Thr Tyr Ser
545                 550                 555                 560
Phe Thr Ile Arg Ala Ser Thr Ala Lys Gly Phe Gly Pro Pro Ala Thr
                565                 570                 575
Asn Gln Phe Thr Thr Lys Ile Ser Ala Pro Ser Met Pro Ala Tyr Glu
            580                 585                 590
Leu Glu Thr Pro Leu Asn Gln Thr Asp Asn Thr Val Thr Val Met Leu
        595                 600                 605
Lys Pro Ala His Ser Arg Gly Ala Pro Val Ser Val Tyr Gln Ile Val
    610                 615                 620
Val Glu Glu Glu Arg Pro Arg Arg Thr Lys Lys Thr Thr Glu Ile Leu
625                 630                 635                 640
Lys Cys Tyr Pro Val Pro Ile His Phe Gln Asn Ala Ser Leu Leu Asn
                645                 650                 655
```

```
Ser Gln Tyr Tyr Phe Ala Ala Glu Phe Pro Ala Asp Ser Leu Gln Ala
            660                 665                 670

Ala Gln Pro Phe Thr Ile Gly Asp Asn Lys Thr Tyr Asn Gly Tyr Trp
        675                 680                 685

Asn Thr Pro Leu Leu Pro Tyr Lys Ser Tyr Arg Ile Tyr Phe Gln Ala
    690                 695                 700

Ala Ser Arg Ala Asn Gly Glu Thr Lys Ile Asp Cys Val Gln Val Ala
705                 710                 715                 720

Thr Lys Gly Ala Ala Thr Pro Lys Pro Val Pro Glu Pro Glu Lys Gln
                725                 730                 735

Thr Asp His Thr Val Lys Ile Ala Gly Val Ile Ala Gly Ile Leu Leu
            740                 745                 750

Phe Val Ile Ile Phe Leu Gly Val Val Leu Val Met Lys Lys Arg Lys
        755                 760                 765

Leu Ala Lys Lys Arg Lys Glu Thr Met Ser Ser Thr Arg Gln Glu Met
    770                 775                 780

Thr Val Met Val Asn Ser Met Asp Lys Ser Tyr Ala Glu Gln Gly Thr
785                 790                 795                 800

Asn Cys Asp Glu Ala Phe Ser Phe Met Asp Thr His Asn Leu Asn Gly
                805                 810                 815

Arg Ser Val Ser Ser Pro Ser Ser Phe Thr Met Lys Thr Asn Thr Leu
            820                 825                 830

Ser Thr Ser Val Pro Asn Ser Tyr Tyr Pro Asp Pro Phe Val Pro Thr
        835                 840                 845

Ala Ile Leu Val Pro Ile Asn Asp Glu Thr His Thr Met Ala Ser Asp
850                 855                 860

Thr Ser Ser Leu Val Gln Ser His Thr Tyr Lys Lys Arg Glu Pro Ala
865                 870                 875                 880

Asp Val Pro Tyr Gln Thr Gly Gln Leu His Pro Ala Ile Arg Val Ala
                885                 890                 895

Asp Leu Leu Gln His Ile Thr Gln Met Lys Cys Ala Glu Gly Tyr Gly
            900                 905                 910

Phe Lys Glu Glu Tyr Glu Ser Phe Phe Glu Gly Gln Ser Ala Pro Trp
        915                 920                 925

Asp Ser Ala Lys Lys Asp Glu Asn Arg Met Lys Asn Arg Tyr Gly Asn
930                 935                 940

Ile Ile Ala Tyr Asp His Ser Arg Val Arg Leu Gln Thr Ile Glu Gly
945                 950                 955                 960

Asp Thr Asn Ser Asp Tyr Ile Asn Gly Asn Tyr Ile Asp Gly Tyr His
                965                 970                 975

Arg Pro Asn His Tyr Ile Ala Thr Gln Gly Pro Met Gln Glu Thr Ile
            980                 985                 990

Tyr Asp Phe Trp Arg Met Val Trp His Glu Asn Thr Ala Ser Ile Ile
        995                 1000                1005

Met Val Thr Asn Leu Val Glu Val Gly Arg Val Lys Cys Cys Lys
    1010                1015                1020

Tyr Trp Pro Asp Asp Thr Glu Ile Tyr Lys Asp Ile Lys Val Thr
    1025                1030                1035

Leu Ile Glu Thr Glu Leu Leu Ala Glu Tyr Val Ile Arg Thr Phe
    1040                1045                1050

Ala Val Glu Lys Arg Gly Val His Glu Ile Arg Glu Ile Arg Gln
    1055                1060                1065
```

```
Phe His Phe Thr Gly Trp Pro Asp His Gly Val Pro Tyr His Ala
1070                1075                1080

Thr Gly Leu Leu Gly Phe Val Arg Gln Val Lys Ser Lys Ser Pro
1085                1090                1095

Pro Ser Ala Gly Pro Leu Val Val His Cys Ser Ala Gly Ala Gly
1100                1105                1110

Arg Thr Gly Cys Phe Ile Val Ile Asp Ile Met Leu Asp Met Ala
1115                1120                1125

Glu Arg Glu Gly Val Val Asp Ile Tyr Asn Cys Val Arg Glu Leu
1130                1135                1140

Arg Ser Arg Arg Val Asn Met Val Gln Thr Glu Glu Gln Tyr Val
1145                1150                1155

Phe Ile His Asp Ala Ile Leu Glu Ala Cys Leu Cys Gly Asp Thr
1160                1165                1170

Ser Val Pro Ala Ser Gln Val Arg Ser Leu Tyr Tyr Asp Met Asn
1175                1180                1185

Lys Leu Asp Pro Gln Thr Asn Ser Ser Gln Ile Lys Glu Glu Phe
1190                1195                1200

Arg Thr Leu Asn Met Val Thr Pro Thr Leu Arg Val Glu Asp Cys
1205                1210                1215

Ser Ile Ala Leu Leu Pro Arg Asn His Glu Lys Asn Arg Cys Met
1220                1225                1230

Asp Ile Leu Pro Pro Asp Arg Cys Leu Pro Phe Leu Ile Thr Ile
1235                1240                1245

Asp Gly Glu Ser Ser Asn Tyr Ile Asn Ala Ala Leu Met Asp Ser
1250                1255                1260

Tyr Lys Gln Pro Ser Ala Phe Ile Val Thr Gln His Pro Leu Pro
1265                1270                1275

Asn Thr Val Lys Asp Phe Trp Arg Leu Val Leu Asp Tyr His Cys
1280                1285                1290

Thr Ser Val Val Met Leu Asn Asp Val Asp Pro Ala Gln Leu Cys
1295                1300                1305

Pro Gln Tyr Trp Leu Glu Asn Gly Val His Arg His Gly Pro Ile
1310                1315                1320

Gln Val Glu Phe Val Ser Ala Asp Leu Glu Glu Asp Ile Ile Ser
1325                1330                1335

Arg Ile Phe Arg Ile Tyr Asn Ala Ala Arg Pro Gln Asp Gly Tyr
1340                1345                1350

Arg Met Val Gln Gln Phe Gln Phe Leu Gly Trp Pro Met Tyr Arg
1355                1360                1365

Asp Thr Pro Val Ser Lys Arg Ser Phe Leu Lys Leu Ile Arg Gln
1370                1375                1380

Val Asp Lys Trp Gln Glu Glu Tyr Asn Gly Gly Glu Gly Arg Thr
1385                1390                1395

Val Val His Cys Leu Asn Gly Gly Gly Arg Ser Gly Thr Phe Cys
1400                1405                1410

Ala Ile Ser Ile Val Cys Glu Met Leu Arg His Gln Arg Thr Val
1415                1420                1425

Asp Val Phe His Ala Val Lys Thr Leu Arg Asn Asn Lys Pro Asn
1430                1435                1440
```

Met Val Asp Leu Leu Asp Gln Tyr Lys Phe Cys Tyr Glu Val Ala
    1445                1450                1455

Leu Glu Tyr Leu Asn Ser Gly
    1460                1465

<210> SEQ ID NO 2
<211> LENGTH: 477
<212> TYPE: PRT
<213> ORGANISM: Homo sapiens

<400> SEQUENCE: 2

Met Arg Gly Leu Gly Thr Cys Leu Ala Thr Leu Ala Gly Leu Leu
1               5                   10                  15

Thr Ala Ala Gly Glu Thr Phe Ser Gly Gly Cys Leu Phe Asp Pro
                20                  25                  30

Tyr Ser Thr Cys Gly Tyr Ser Gln Ser Glu Gly Asp Asp Phe Asn Trp
                35                  40                  45

Glu Gln Val Asn Thr Leu Thr Lys Pro Thr Ser Asp Pro Trp Met Pro
50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Lys Ser Asn Ser Pro Pro Gly
                100                 105                 110

Leu Leu Asn Val Tyr Val Lys Val Asn Asn Gly Pro Leu Gly Asn Pro
                115                 120                 125

Ile Trp Asn Ile Ser Gly Asp Pro Thr Arg Thr Trp Asn Arg Ala Glu
                130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
                180                 185                 190

Asn Val Glu Val Asn Ala Gly Gln Phe Ala Thr Phe Gln Cys Ser Ala
                195                 200                 205

Ile Gly Arg Thr Val Ala Gly Asp Arg Leu Trp Leu Gln Gly Ile Asp
                210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
                260                 265                 270

Tyr Ala Glu Leu Val Val Lys Glu Pro Pro Val Pro Ile Ala Pro Pro
                275                 280                 285

Gln Leu Ala Ser Val Gly Ala Thr Tyr Leu Trp Ile Gln Leu Asn Ala
                290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
                340                 345                 350

```
Val Leu Leu Thr Arg Pro Gly Glu Gly Gly Thr Gly Ser Pro Gly Pro
            355                 360                 365

Ala Leu Arg Thr Arg Thr Lys Cys Ala Asp Pro Met Arg Gly Pro Arg
370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Cys Tyr Gln Val Gly Gln Glu Gln Val Arg Glu Glu
            420                 425                 430

Val Ser Trp Asp Thr Glu Asn Ser His Pro Gln His Thr Ile Thr Asn
            435                 440                 445

Leu Ser Pro Tyr Thr Asn Val Ser Val Lys Leu Ile Leu Met Asn Pro
450                 455                 460

Glu Gly Arg Lys Glu Ser Gln Glu Leu Ile Val Gln Thr
465                 470                 475
```

<210> SEQ ID NO 3
<211> LENGTH: 280
<212> TYPE: PRT
<213> ORGANISM: Homo sapiens

<400> SEQUENCE: 3

```
Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
                20                  25                  30

Tyr Ser Thr Cys Gly Tyr Ser Gln Ser Glu Gly Asp Asp Phe Asn Trp
            35                  40                  45

Glu Gln Val Asn Thr Leu Thr Lys Pro Thr Ser Asp Pro Trp Met Pro
50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
                100                 105                 110

Leu Leu Asn Val Tyr Val Lys Val Asn Asn Gly Pro Leu Gly Asn Pro
            115                 120                 125

Ile Trp Asn Ile Ser Gly Asp Pro Thr Arg Thr Trp Asn Arg Ala Glu
130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255
```

Lys Tyr Arg Cys Met Ile Arg Thr Glu Gly Gly Val Gly Ile Ser Asn
            260                 265                 270

Tyr Ala Glu Leu Val Val Lys Glu
        275                 280

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

Glu Thr Phe Ser Gly Gly Cys Leu Phe Asp Glu Pro Tyr Ser Thr Cys
1               5                   10                  15

Gly Tyr Ser Gln
            20

<210> SEQ ID NO 5
<211> LENGTH: 19
<212> TYPE: PRT
<213> ORGANISM: Artificial Sequence
<220> FEATURE:
<223> OTHER INFORMATION: Synthetic peptide

<400> SEQUENCE: 5

Glu Gly Asp Asp Phe Asn Trp Glu Gln Val Asn Thr Leu Thr Lys Pro
1               5                   10                  15

Thr Ser Asp

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide

<400> SEQUENCE: 6

Thr Pro His Phe Leu Arg Ile Gln Asn Val Glu Val Asn Ala Gly Gln
1               5                   10                  15

Phe Ala Thr

<210> SEQ ID NO 7
<211> LENGTH: 18
<212> TYPE: PRT
<213> ORGANISM: Artificial Sequence
<220> FEATURE:
<223> OTHER INFORMATION: Synthetic peptide

<400> SEQUENCE: 7

Gly Ile Asp Val Arg Asp Ala Pro Leu Lys Glu Ile Lys Val Thr Ser
1               5                   10                  15

Ser Arg

<210> SEQ ID NO 8
<211> LENGTH: 621
<212> TYPE: PRT
<213> ORGANISM: Artificial Sequence
<220> FEATURE:
<223> OTHER INFORMATION: Synthetic Construct

<400> SEQUENCE: 8

```
Met Arg Thr Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
            100                 105                 110

Leu Leu Asn Val Tyr Val Lys Val Asn Asn Gly Pro Leu Gly Asn Pro
        115                 120                 125

Ile Trp Asn Ile Ser Gly Asp Pro Thr Arg Thr Trp Asn Arg Ala Glu
    130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
    210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
            260                 265                 270

Tyr Ala Glu Leu Val Val Lys Glu Pro Pro Val Pro Ile Ala Pro Pro
        275                 280                 285

Gln Leu Ala Ser Val Gly Ala Thr Tyr Leu Trp Ile Gln Leu Asn Ala
    290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
            340                 345                 350

Val Leu Leu Thr Arg Pro Gly Glu Gly Gly Thr Gly Ser Pro Gly Pro
        355                 360                 365

Ala Leu Arg Thr Arg Thr Lys Cys Ala Asp Pro Met Arg Gly Pro Arg
    370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415
```

```
Val His Tyr Cys Tyr Gln Val Gly Gly Gln Glu Gln Val Arg Glu Glu
            420                 425                 430

Val Ser Trp Asp Thr Glu Asn Ser His Pro Gln His Thr Ile Thr Asn
        435                 440                 445

Leu Ser Pro Tyr Thr Asn Val Ser Val Lys Leu Ile Leu Met Asn Pro
    450                 455                 460

Glu Gly Arg Lys Glu Ser Gln Glu Leu Ile Val Gln Thr Asp Glu Asp
465                 470                 475                 480

Leu Pro Gly Ala Val Pro Thr Glu Ser Ile Gln Gly Ser Thr Phe Glu
                485                 490                 495

Glu Lys Ile Phe Leu Gln Trp Arg Glu Pro Thr Gln Thr Tyr Gly Val
            500                 505                 510

Ile Thr Leu Tyr Glu Ile Thr Tyr Lys Ala Val Ser Ser Phe Asp Pro
        515                 520                 525

Glu Ile Asp Leu Ser Asn Gln Ser Gly Arg Val Ser Lys Leu Gly Asn
    530                 535                 540

Glu Thr His Phe Leu Phe Phe Gly Leu Tyr Pro Gly Thr Thr Tyr Ser
545                 550                 555                 560

Phe Thr Ile Arg Ala Ser Thr Ala Lys Gly Phe Gly Pro Pro Ala Thr
                565                 570                 575

Asn Gln Phe Thr Thr Lys Ile Ser Ala Pro Ser Met Pro Ala Tyr Glu
            580                 585                 590

Leu Glu Thr Pro Leu Asn Gln Thr Asp Asn Thr Val Thr Val Met Leu
        595                 600                 605

Lys Pro Ala His Ser Arg Gly Ala Pro Val Ser Val Tyr
    610                 615                 620

<210> SEQ ID NO 9
<211> LENGTH: 226
<212> TYPE: PRT
<213> ORGANISM: Homo sapiens

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly
225

<210> SEQ ID NO 10
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 10

Gly Phe Thr Gln Pro Glu Thr Gly Thr Asp Asn Asp Leu Trp Ser Val
1               5                   10                  15

Asp Asn Glu Lys
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 11

Gly Glu Gly Asp Asp Phe Asn Trp Glu Gln Val Asn Thr Leu Thr Lys
1               5                   10                  15

Pro Thr Ser Asp
            20

<210> SEQ ID NO 12
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 12

Cys Gly Glu Gly Asp Asp Phe Asn Trp Glu Gln Val Asn Thr Leu Thr
1               5                   10                  15

Lys Pro Thr Ser Asp
            20
```